United States Patent [19]

Conrow

[11] Patent Number: 4,632,104
[45] Date of Patent: Dec. 30, 1986

[54] DEVICE FOR RELIEF OF HEADACHES

[76] Inventor: Robert P. Conrow, 120 Caribe Isle, Novato, Calif. 94947

[21] Appl. No.: 776,602

[22] Filed: Sep. 16, 1985

[51] Int. Cl.⁴ ............................................. A61F 13/12
[52] U.S. Cl. ........................................... 128/163; 2/13
[58] Field of Search .................. 128/97, 76 R, 76 B, 128/76.5, 163, 151, 152; 2/15, 11, 12, 13, 425, 426, 450, DIG. 11

[56] References Cited

U.S. PATENT DOCUMENTS

| | | | |
|---|---|---|---|
| 1,062,399 | 5/1913 | Hess et al. | 128/76 B |
| 2,670,737 | 3/1954 | Cantor | 128/152 |
| 2,946,394 | 7/1960 | Smith | 128/151 UX |

FOREIGN PATENT DOCUMENTS 2476332  8/1981  France ....................................... 2/15

*Primary Examiner*—Gregory E. McNeill
*Attorney, Agent, or Firm*—Melvin R. Stidham

[57] ABSTRACT

The disclosure is of a device for applying tension to the ear from the forward part of the skull or cranium so as to pull the ear and bring the temporal bone on which it is carried into external rotation to relieve pressure on the blood vessels and nerves carried within the temporal bone and other parts of the skull.

6 Claims, 5 Drawing Figures

DEVICE FOR RELIEF OF HEADACHES

BACKGROUND OF THE INVENTION

Headaches are frequently caused by strain and tension on nerves, as well as on blood and lymph vessels within the cranium. In the past, appliances have been devised for the cure of headaches by application of pressure to points on the cranium in order to interrupt or restrict blood flow in local areas. Appliances of this type are described and claimed in U.S. Pat. Nos. 763,814 granted June 28, 1904, 841,714 granted Jan. 22, 1907 and 937,596 granted Oct. 19, 1909. It is now believed that headache relief can be better achieved by relieving pressure to improve circulation and to stimulate the flow of cerebral spinal fluid.

Such increased circulation can be accomplished by outward rotation of the temporal bone on either or both sides of the skull. External rotation of the temporal bone is also found to relieve symptoms of vertigo, motion sickness, dizziness, pregnancy nausea and the like, which symptoms are problems of the semi-lunar canals of the ear contained within the temporal bone.

The brain and its components are surrounded and separated by dural membranes, which also attach to various bones of the skull. The delicate state of balance of nerves and blood vessels lying within these dural folds can be disturbed by a shift in the position of the bone to which they are attached. It is, therefore, desirable to restore the delicate state of balance and equilibrium of the dural membranes when necessary to do so.

OBJECTS OF THE INVENTION

It is an object of this invention to provide a device for relief of headaches.

It is a further object of this invention to provide a device for relief of symptoms of vertigo, motion sickness, dizziness, pregnancy nausea and the like.

It is a further object of this invention to provide a device for rotating the temporal bone on the side of the skull to increase flow of blood and stimulate cerebral spinal fluid.

Other objects and advantages of this invention will become apparent from the description to follow, particularly when read in conjunction with the accompanying drawings.

SUMMARY OF THE INVENTION

In carrying out this invention, I provide a device to grip and pull the ear, and thereby rotate the temporal bone on which it is carried outwardly. In one form, the device may comprise a headband or similar means secured to the skull as an anchor member and a tension member of elastic or the like is secured to the headband to pull on the ear. The ear may be gripped by any suitable means, such as, an earplug inserted into the external ear canal, a movable earpiece attached to the frame of a pair of glasses.

DESCRIPTION OF PREFERRED EMBODIMENTS

Figure 1:
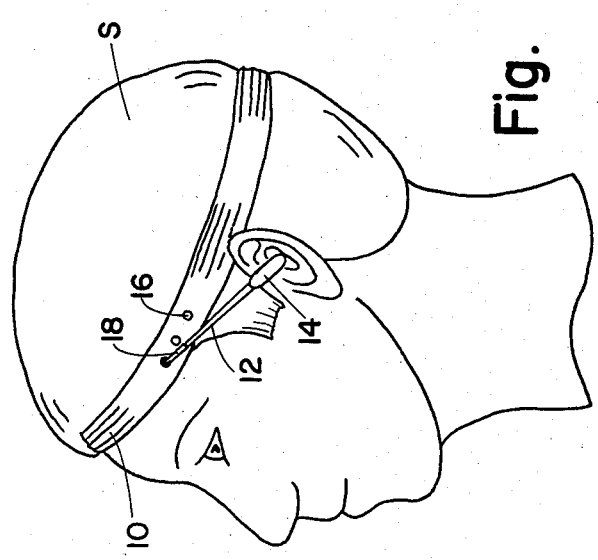
FIG. 1 is a view in perspective of one embodiment of this invention.

The Embodiment of FIG. 1

Here, a headband 10 of elastic, knitted fibers or the like, is secured around the skull S of the subject to function as the anchor for the elastic tension member 12. The elastic tension member 12 carries an earpiece 14 at the distal end thereof to be inserted into the external ear canal to pull the ear and temporal bone therewith into outward rotation, pivoting it about the petrous portion of the temporal bone in advance of the ear. A series of holes 16 may be provided in each side of the headband 10 to permit adjustment of the amount of tension applied by the elastic tension member 12 on each side of the skull S by engaging a selected hole 16 with a hook 18 on the end of the tension member 12. Means may also be provided to adjust tensile pull of the tension member 12.

Figure 2:
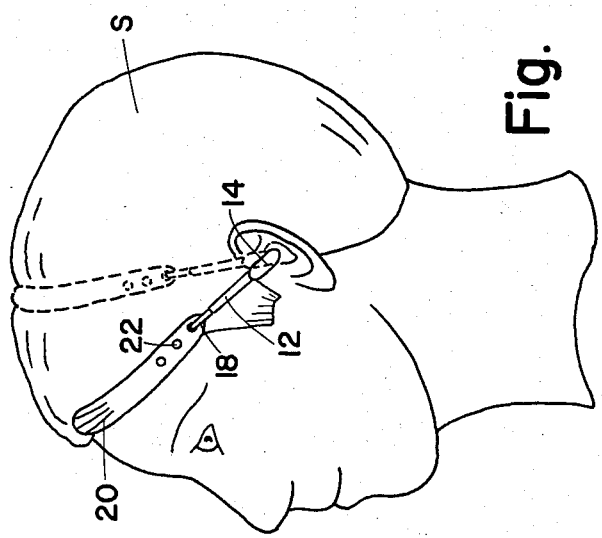
FIG. 2 is a view in perspective of a second embodiment of this invention involving a partial headband.

The Embodiment of FIG. 2

In this embodiment, a partial headband 20 carries a tension member 12 at each end thereof with the earplug 14 carried thereon to be inserted into the external ear canal of the subject S. Hence, tension is applied to both ears simultaneously, pulling both temporal bones into outward or external rotation. As shown, the partial headband 20 may be located in different positions on the skull to control the direction of tension and a series of holes 22 may be provided at each end to receive the clip or hook 18 on the tension member and thereby regulate the amount of tension. In this embodiment, as in FIG. 1, the partial headband 20 may also be of an elastic material to increase the tension on the temporal bone.

Figure 3:
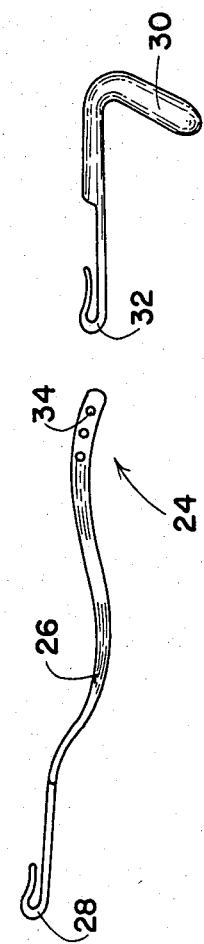
FIG. 3 is an enlarged view in perspective of an adjustable tension member.

The Embodiment of FIG. 3

Figure 4:
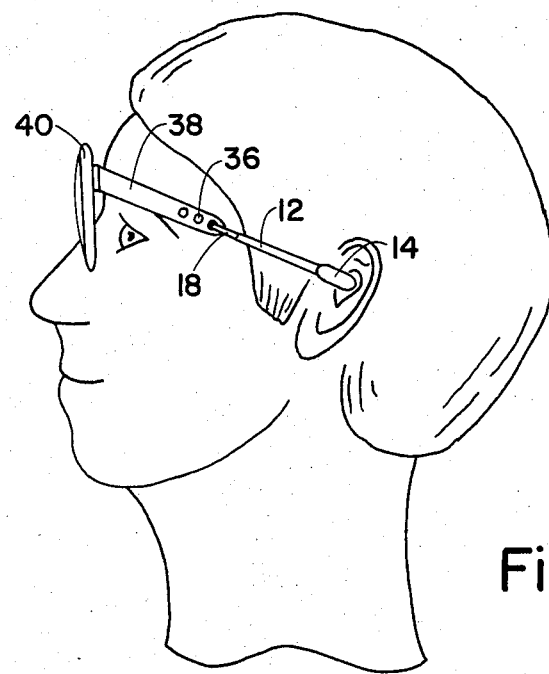
FIG. 4 is a view in perspective of a third embodiment of this invention.

Here there is shown an adjustable tension member 24 that is applicable to the Embodiment of FIGS. 1, 2 and 4. It comprises an elastic band 26 carrying a hook 28 that is engagable with the adjustment holes 16 (FIG. 1) or 22 (FIG. 2). Similarly, the ear plug 30 carries a hook 32 that engages a selected hole 34 in the elastic band 26 for further adjustment of the tension.

The Embodiment of FIG. 4

In this embodiment, an earplug 14 on tension member 12 is inserted into the outer ear canal and the hook 18 on the tension member 12 is secured into a selected opening 36 in the frame 38 of a pair of eyeglasses 40 whereby the eyeglasses 40 function as the anchor member to pull against, again placing the temporal bone in outward or external rotation for relief of pressure against blood vessels and to stimulate flow of cerebral spinal fluid. Like tension members 12 may be attached to both sides of the eyeglass frame 38.

Figure 5:
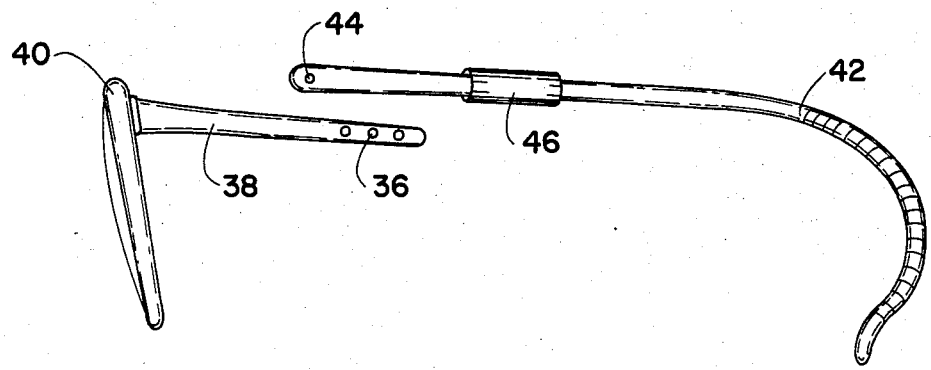
FIG. 5 is a view in prespective of still another embodiment of this invention.

The Embodiment of FIG. 5

In this embodiment, the tension member takes the form of an earpiece 42 of spring steel or the like that extends around the outside of the ear to apply tension and induce external rotation. The tension member may be secured by engagement of a pin 44 in a selected hole in the side band 38 of a pair of eyeglasses 40. A sleeve 46 may be slipped over the engaged pin 44 to lock it against inadvertent disengagement.

While this invention has been described in conjunction with preferred embodiments thereof, it is obvious that modifications and changes therein may be made by those skilled in the art to which it pertains without departing from the spirit and scope of this invention, as defined by the claims appended hereto.

What is claimed is:

1. A device for relief of discomfort comprising:
   a base member adapted to be fixed on the forward portion of the skull of a human subject;
   an earpiece for gripping the ear of said subject; and
   a tension member attached at one end thereof to said base member and carrying said earpiece on the other end thereof, said tension member being extended within its elastic limits to pull said ear forward.

2. The device defined by claim 1 wherein:
   said earpiece is a plug to be inserted into the outer ear canal.

3. The device defined by claim 1 wherein:
   said earpiece is adapted to hook over and around the ear.

4. The device defined by claim 1 including:
   means for adjusting the tension applied by said tension member.

5. The device defined by claim 1 wherein:
   said base member is a headband.

6. The device defined by claim 1 wherein said base member comprises:
   the frame of a pair of eyeglasses.

* * * * *